(12) United States Patent
Kawamura et al.

(10) Patent No.: US 10,072,117 B2
(45) Date of Patent: Sep. 11, 2018

(54) LACTIC ACID PRODUCTION METHOD

(71) Applicant: Toray Industries, Inc., Tokyo (JP)

(72) Inventors: Kenji Kawamura, Kamakura (JP);
Masateru Ito, Kamakura (JP);
Katsushige Yamada, Kamakura (JP)

(73) Assignee: Toray Industries, Inc. (JP)

( * ) Notice: Subject to any disclaimer, the term of this patent is extended or adjusted under 35 U.S.C. 154(b) by 382 days.

(21) Appl. No.: 14/399,992

(22) PCT Filed: May 21, 2013

(86) PCT No.: PCT/JP2013/064004
§ 371 (c)(1),
(2) Date: Nov. 10, 2014

(87) PCT Pub. No.: WO2013/176101
PCT Pub. Date: Nov. 28, 2013

(65) Prior Publication Data
US 2015/0112041 A1 Apr. 23, 2015

(30) Foreign Application Priority Data
May 22, 2012 (JP) .................. 2012-116276

(51) Int. Cl.
C08G 63/06 (2006.01)
C07C 51/44 (2006.01)
C07C 51/47 (2006.01)
C12P 7/56 (2006.01)

(52) U.S. Cl.
CPC .............. *C08G 63/06* (2013.01); *C07C 51/44* (2013.01); *C07C 51/47* (2013.01); *C12P 7/56* (2013.01)

(58) Field of Classification Search
None
See application file for complete search history.

(56) References Cited

U.S. PATENT DOCUMENTS

| 3,202,705 | A | * | 8/1965 | Powell | .................... C07C 51/47 |
| | | | | | 435/139 |
| 5,210,294 | A | | 5/1993 | Mantovani et al. | |
| 5,503,750 | A | | 4/1996 | Russo et al. | |
| 6,489,508 | B1 | | 12/2002 | Van Gansbeghe et al. | |
| 2005/0112737 | A1 | * | 5/2005 | Liu | ........................ C12N 1/18 |
| | | | | | 435/139 |
| 2007/0161098 | A1 | | 7/2007 | Yamaguchi et al. | |
| 2009/0104675 | A1 | | 4/2009 | Yamaguchi et al. | |
| 2009/0199460 | A1 | * | 8/2009 | Munson | ................. B01D 15/00 |
| | | | | | 44/308 |

FOREIGN PATENT DOCUMENTS

| CN | 1754897 | | 4/2006 |
| JP | 52-97910 | | 8/1977 |
| JP | 52-105284 | | 9/1977 |
| JP | 62-201606 | | 9/1987 |
| JP | 2006-094813 | | 4/2006 |
| JP | 2011-026394 | | 2/2011 |
| JP | 2011103879 A | * | 6/2011 |
| JP | 2012-12322 | | 1/2012 |

OTHER PUBLICATIONS

Supplementary European Search Report dated Jan. 4, 2016 of corresponding European Application No. 13793821.3.
Russian Office Action dated Aug. 14, 2017, of corresponding Russian Application No. 2014151793/04, along with an English translation.

* cited by examiner

*Primary Examiner* — Randy P Gulakowski
*Assistant Examiner* — Kara Brady Boyle
(74) *Attorney, Agent, or Firm* — DLA Piper LLP (US)

(57) ABSTRACT

A method of producing lactic acid includes removing glycerol from an aqueous lactic acid solution containing glycerol as an impurity using an ion-exchange resin. The lactic acid can be separated simply and at low cost from an aqueous lactic acid solution containing glycerol as an impurity.

7 Claims, No Drawings

LACTIC ACID PRODUCTION METHOD

TECHNICAL FIELD

This disclosure relates to a method of producing lactic acid by separation of lactic acid from glycerol in an aqueous lactic acid solution.

BACKGROUND

Lactic acid is widely applied not only to uses such as food and pharmaceuticals, but also to industrial uses as a monomer material for biodegradable plastics, and increasingly demanded. 2-Hydroxypropionic acid, that is, lactic acid, is known to be produced by fermentation by microorganisms, wherein the microorganisms convert substrates containing carbohydrates such as glucose into lactic acid. Lactic acid is divided into optical isomers, the (L)-isomer and the (D)-isomer, based on the configuration of the substituent to the carbon at the α position of carbonyl group. By appropriately selecting the microorganism for microbial fermentation, (L)- or (D)-lactic acid can be selectively produced, or lactic acid as a mixture of the (L)-isomer and the (D)-isomer (racemic body) can be produced.

Production of lactic acid by microbial fermentation is generally carried out while a pH appropriate for the microbial fermentation is maintained by addition of an alkaline substance (e.g., calcium hydroxide) to the culture medium. Most of the lactic acid produced as an acidic substance by the microbial fermentation is made to be present in the fermented broth as a lactic acid salt (e.g., calcium lactate) by the addition of an alkaline substance. When lactic acid is used as monomers for a plastic, the lactic acid to be used is preferably free lactic acid obtained by adding an acidic substance (e.g., sulfuric acid) to the fermented broth after completion of the fermentation. However, the lactic acid fermented broth obtained by microbial fermentation contains, other than lactic acid as the product of interest, organic acids and salts thereof, proteins, amino acids, and nonionic compounds such as glycerol, as impurities. When lactic acid is used as monomers for a plastic, the lactic acid needs to be separated from these impurities.

For example, as a method of removing impurities from an aqueous lactic acid solution derived from a lactic acid fermented broth obtained by microbial fermentation, Japanese Translated PCT Patent Application Laid-Open No. 2001-506274 describes a method in which an aqueous lactic acid solution is subjected to ion-exchange treatment to remove ionic components, and the processed liquid is then subjected to distillation. As a method of removing nonionic impurities, JP 2006-75133 A describes a method in which lactic acid contained in an aqueous lactic acid solution is adsorbed to, and then eluted from, an ion-exchange resin to remove glycerol, which is an impurity contained in the aqueous lactic acid solution (however, Examples in JP '133 do not describe an example in which lactic acid is adsorbed to, and then eluted from, an ion-exchange resin).

To separate lactic acid from glycerol, which is a nonionic impurity contained in an aqueous lactic acid solution, there is a method in which, as described above, lactic acid contained in the aqueous lactic acid solution is adsorbed to, and then eluted from, an ion-exchange resin to remove the impurity, glycerol. However, since allowing a large amount of lactic acid to be adsorbed to an ion-exchange resin requires a large amount of the ion-exchange resin, it is thought that there are problems such as requirement of large equipment.

It could therefore be helpful to provide a method of separating lactic acid from an aqueous lactic acid solution containing glycerol as an impurity, which method enables simple and low-cost production of lactic acid in which glycerol is reduced.

SUMMARY

We discovered that glycerol, which is a nonionic impurity contained in an aqueous lactic acid solution, can be adsorbed to an ion-exchange resin.

We provide (1) to (6) below:
(1) A method of producing lactic acid, the method comprising the step of removing glycerol from an aqueous lactic acid solution containing glycerol as an impurity using an ion-exchange resin.
(2) The method of producing lactic acid according to (1), wherein the ion-exchange resin is a strong acid ion-exchange resin.
(3) The method of producing lactic acid according to (1) or (2), wherein the lactic acid concentration in the aqueous lactic acid solution is not less than 20% by weight.
(4) The method of producing lactic acid according to any one of (1) to (3), comprising the step of distilling the aqueous lactic acid solution after the removal of glycerol using the ion-exchange resin.
(5) A method of producing polylactic acid, the method comprising using as a raw material the lactic acid obtained by the method of producing lactic acid according to any one of (1) to (4).
(6) A method of producing polylactic acid, the method comprising subjecting the lactic acid obtained by the method of producing lactic acid according to any one of (1) to (4) to direct dehydration polycondensation.

Glycerol contained as an impurity in an aqueous lactic acid solution can be reduced effectively and at low cost by a simple operation, and lactic acid suitable for production of polylactic acid excellent in the melting point and thermostability can be produced.

DETAILED DESCRIPTION

The method of producing lactic acid comprises the step of removing glycerol from an aqueous lactic acid solution containing glycerol as an impurity using an ion-exchange resin.

The "aqueous lactic acid solution containing glycerol as an impurity" means an aqueous solution containing lactic acid as a main component, and glycerol as an impurity. The origin of the aqueous lactic acid solution is not limited as long as the solution contains glycerol as an impurity, and the solution may be an aqueous solution of lactic acid obtained by organic synthesis, or may be a lactic acid fermentation culture liquid per se obtained by microbial fermentation or a lactic acid fermentation culture liquid processed through a plurality of separation/purification steps. Since lactic acid is an ionic substance, lactic acid may be present as free lactic acid, as a lactic acid salt, or as both of these in an equilibrium state, in an aqueous lactic acid solution containing glycerol as an impurity. As described later, the effect of removal of glycerol is high in the cases where lactic acid is present as free lactic acid. Lactic acid and glycerol contained in an aqueous lactic acid solution can be quantified by high-performance liquid chromatography (HPLC).

In the step of removing glycerol contained in an aqueous lactic acid solution using an ion-exchange resin, glycerol contained in the aqueous lactic acid solution described above is adsorbed to an ion-exchange resin. An ion-exchange resin is a synthetic resin, and has a structure that ionizes as an ionic group in a part of the molecular structure. The resin therefore shows ion exchange action with ionic components in a solvent. Thus, in general, ion-exchange resins are used for the purpose of adsorption of ionic components in solutions. Glycerol, which is a nonionic component, in an aqueous lactic acid solution, which is a solution having high polarity, adsorbs to an ion-exchange resin.

The ion-exchange resin is not limited, and may be a known resin. Specific examples of the ion-exchange resin include "Amberlite" (registered trademark) (manufactured by The Dow Chemical Company), "Diaion" (registered trademark) (manufactured by Mitsubishi Chemical Corporation) and "Duolite" (registered trademark) (manufactured by Rohm and Haas Company), which are commercially available. The ion-exchange resin may be any of acidic resins (cation-exchange resins), basic resins (anion-exchange resins) and their salts. In particular, strong acid ion-exchange resins are preferred since they are excellent in glycerol adsorption capacity, and H-type strong acid ion-exchange resins are especially preferred. These ion-exchange resins may be either the so-called "gel-type" resins or "porous-type" resins. Specific examples of the strong acid ion-exchange resins include: "Diaion" (registered trademark) SK1B, SK1BH, SK110, SK112, PK216, PK216H, PK218, PK220, PK228, PK228H, UBK08, UBK10, UBK12, UBK530, UBK550, UBK535 and UBK555, manufactured by Mitsubishi Chemical Corporation; "Amberlite" (registered trademark) IR120B Na, IR120 H, IR124 Na, 200CT Na, 200CT H, 252 Na and 252 Na, manufactured by The Dow Chemical Company; and "Duolite" (registered trademark) C20J, C20LF, C255LFH, C26A and C26TRH, manufactured by Rohm and Haas Company.

The method of contacting the aqueous lactic acid solution with the ion-exchange resin may be either the batch method (stirred tank method) or the column method (fixed-bed flow method). In view of operability, the column method is preferred. The flow rate of the aqueous lactic acid solution in cases of ion-exchange treatment using an ion-exchange resin column is not limited, and may usually be a flow rate that can attain a space velocity (SV) per unit volume of the ion-exchange resin of 0.1 to 20 $hr^{-1}$. The temperature at which the aqueous lactic acid solution is brought into contact with the ion-exchange resin column is not limited, and the column can be preferably used at normal temperature.

The ion-exchange resin used for removal of glycerol can be regenerated by washing with water. Regeneration of an ion-exchange resin that adsorbed an ion component usually requires washing with a liquid reagent such as an acid or alkali. In contrast, an ion-exchange resin that adsorbed glycerol, which is a nonionic component, can be regenerated by washing with water having high polarity. Thus, the cost of the reagent liquid required for regeneration of the ion-exchange resin can be reduced. The water to be used for resin regeneration is not limited. Since, when water containing a large amount of an ionic component is used, the ionic component causes adsorption of the ionic component to functional groups on the surface of the ion-exchange resin, resulting in a decreased glycerol adsorption effect. Thus, washing using deionized water can be preferably applied.

When the aqueous lactic acid solution to be provided for the step using an ion-exchange resin is a lactic acid fermented broth obtained by microbial fermentation, the fermented broth generally contains an alkaline substance added for adjustment of the pH during the culture. Lactic acid in the lactic acid fermented broth is therefore usually present as a lactic acid salt. In such cases, as a pretreatment before the ion-exchange resin treatment of the aqueous lactic acid solution, the lactic acid salt in the lactic acid fermented broth is preferably converted to free lactic acid. Specific examples of the lactic acid salt include lithium lactate, sodium lactate, potassium lactate, calcium lactate, magnesium lactate, aluminum lactate and ammonium lactate, and mixtures of two or more thereof. When a lactic acid fermentation culture liquid containing lactic acid as a lactic acid salt is treated with an ion-exchange resin, functional groups on the surface of the ion-exchange resin are preferentially used for conversion of the lactic acid salt to free lactic acid, resulting in a decreased glycerol adsorption effect. Thus, by preliminarily preparing an aqueous solution of free lactic acid before the ion-exchange resin treatment, the effect of removing glycerol can be increased.

As a method of obtaining free lactic acid from a lactic acid salt, a method by adding an acidic substance can be employed. The acidic substance is not limited, and sulfuric acid, hydrochloric acid, carbonic acid, phosphoric acid, nitric acid or the like may be used. In view of forming the later-described insoluble salt, sulfuric acid is preferably used. It is preferred to add an acidic substance to the aqueous lactic acid salt solution to cause conversion into an aqueous solution of free lactic acid, while removing the cationic component of lactic acid salt as an insoluble salt. By adding an acidic substance to the aqueous lactic acid salt solution to cause precipitation of the cationic component in the solution and then performing solid-liquid separation by filtration or the like, an aqueous solution of free lactic acid from which cationic ions derived from the lactic acid salt were removed can be obtained. The method of solid-liquid separation of the insoluble salt is not limited, and a method known to those skilled in the art such as filtration through qualitative filter paper or centrifugation may be applied.

Before the treatment of the aqueous lactic acid solution with an ion-exchange resin, the solution may be subjected to the step of removing salts dissolved therein. The removal of salts dissolved in the aqueous lactic acid solution can increase the effect of adsorption of glycerol in the step using an ion-exchange resin. The method of removal of salts dissolved in the aqueous lactic acid solution is not limited, and ion-exchange treatment, membrane filtration treatment or the like may be applied. The ion-exchange treatment herein means removal of ionic components (inorganic salts and the like) in the aqueous lactic acid solution, and the purpose of this treatment is different from the purpose of removal of glycerol as an impurity in the aqueous lactic acid solution using an ion-exchange resin.

The membrane used in the membrane filtration treatment is not limited as long as it allows permeation of lactic acid while blocking salts. The membrane is preferably a nanofiltration membrane. A nanofiltration membrane is also called a nanofilter (nanofiltration membrane, NF membrane), and generally defined as a "membrane that allows permeation of monovalent ions, but blocks divalent ions." The membrane is considered to have fine voids having sizes of about several nanometers, and mainly used to block fine particles, molecules, ions and salts in water. Examples of the material of the nanofiltration membrane which may be used include macromolecular materials such as cellulose acetate polymers, polyamides, polyesters, polyimides and vinyl polymers. The membrane is not limited to a membrane constituted by only one of the materials, and may be a membrane comprising a plurality of membrane materials. In terms of the structure of the membrane, the membrane may be either an asymmetric membrane having a dense layer on at least one side of the membrane, wherein micropores having pore sizes that gradually increase in the direction from the dense layer toward the inside of the membrane or toward the other side of the membrane are present, or a composite membrane having a very thin functional layer formed by another material on the dense layer of the asymmetric membrane. Examples of the composite membrane which may be used include the composite membrane described in JP 62-201606 A, which has a nanofiltration membrane composed of a polyamide functional layer on a support membrane comprising polysulfone as a membrane material.

A nanofiltration membrane is generally used as a spiral-wound membrane element, and the nanofiltration membrane is also preferably used as a spiral-wound membrane element. Specific preferred examples of the nanofiltration membrane element include "GEsepa" (registered trademark), manufactured by GE Osmonics; NF99 and NF99HF, manufactured by Alfa-Laval; NF-45, NF-90, NF-200 and NF-400, manufactured by Filmtec Corporation; and SU-210, SU-220, SU-600 and SU-610, which are nanofiltration membrane elements manufactured by Toray Industries, Inc., having UTC60 manufactured by the same manufacturer.

The concentration of lactic acid in the aqueous lactic acid solution to be subjected to the step using an ion-exchange resin is not limited. When the lactic acid concentration in the aqueous lactic acid solution is less than 20% by weight, inhibition of adsorption of glycerol to the ion-exchange resin occurs due to the high-polarity water. It is therefore preferred to concentrate the solution to a lactic acid concentration of not less than 20% by weight by a concentration operation before the treatment with an ion-exchange resin. On the other hand, when the lactic acid concentration in the aqueous lactic acid solution is more than 90% by weight, the aqueous lactic acid solution has high viscosity, and therefore fluidity and operability of the aqueous lactic acid solution during the ion-exchange resin step are poor. Thus, the ion-exchange resin treatment is preferably carried out at a lactic acid concentration of not more than 90% by weight.

Examples of the method of concentrating the aqueous lactic acid solution include vaporization of water by heating under reduced pressure with a concentrator such as an evaporator, and increasing of the lactic acid concentration using a reverse osmosis membrane. In view of reducing the energy required for the concentration, a concentration method using a reverse osmosis membrane is preferred. The reverse osmosis membrane herein means a filtration membrane that can separate ions and low-molecular-weight molecules by filtration using as a driving force a pressure difference larger than the osmotic pressure of the untreated liquid. The concentration of the aqueous lactic acid solution using a reverse osmosis membrane can be carried out by allowing water in the aqueous lactic acid solution to permeate into the permeate side of the reverse osmosis membrane, thereby obtaining an aqueous lactic acid solution with an increased lactic acid concentration in the feed side.

Examples of the membrane material of the reverse osmosis membrane which may be used for the concentration of the aqueous lactic acid solution include macromolecular materials such as cellulose acetate polymers, polyamides, polyesters, polyimides and vinyl polymers, which are generally commercially available. The membrane is not limited to a membrane constituted by only one of the materials, and may be a membrane comprising a plurality of membrane materials. In terms of the structure of the membrane, the membrane may be either an asymmetric membrane having a dense layer on at least one side of the membrane, wherein micropores having pore sizes that gradually increase in the direction from the dense layer toward the inside of the membrane or toward the other side of the membrane are present, or a composite membrane having a very thin functional layer formed by another material on the dense layer of the asymmetric membrane. Examples of the form of the reverse osmosis membrane which may be used as appropriate include the flat membrane, spiral-wound membrane and hollow fiber membrane.

Specific examples of the reverse osmosis membrane include UTC-70, SU-710, SU-720, SU-720F, SU-710L, SU-720L, SU-720LF, SU-720R, SU-710P, SU-720P, SU-810, SU-820, SU-820L, SU-820FA, SU-610, SU-620, TM800, TM800C, TM800A, TM800H, TM800E and TM800L, which are polyamide reverse osmosis membranes manufactured by Toray Industries, Inc.; SC-L100R, SC-L200R, SC-1100, SC-1200, SC-2100, SC-2200, SC-3100, SC-3200, SC-8100 and SC-8200, which are cellulose acetate reverse osmosis membranes manufactured by Toray Industries, Inc.; NTR-759HR, NTR-729HF, NTR-70SWC, ES10-D, ES20-D, ES20-U, ES15-D, ES15-U and LF10-D, manufactured by Nitto Denko Corporation; RO98pHt, RO99, HR98PP, CE4040C-30D, NF99 and NF99HF, manufactured by Alfa-Laval; GE Sepa, OSMO BEV NF Series, HL Series, Duraslick Series, MUNI NF Series, CK Series, DK Series, Seasoft Series and Duratherm HWS Series, manufactured by GE; SelRO Series, manufactured by KOCH; and BW30-4040, TW30-4040, XLE-4040, LP-4040, LE-4040, SW30-4040, SW30HRLE-4040, NF45, NF90, NF200 and NF400, manufactured by FilmTec Corporation.

Highly pure lactic acid in which glycerol is further reduced can be obtained by further subjecting the aqueous lactic acid solution obtained by the ion-exchange resin step to a distillation step. The lactic acid concentration in the aqueous lactic acid solution to be subjected to the distillation step is not limited, and the aqueous lactic acid solution per se obtained by the ion-exchange resin treatment may be distilled, or the aqueous lactic acid solution may be subjected to treatment using an evaporator or to the above-described concentration step using a reverse osmosis membrane, before the distillation. When the lactic acid concentration in the solution is too low, a large distillation equipment is necessary, while in cases where the concentration is too high, oligomerization may occur, leading to a low yield. Thus, the distillation can be appropriately carried out in cases where the concentration of lactic acid is 50 to 95% by weight, preferably 60 to 90% by weight. The distillation step is carried out under a reduced pressure of not less than 1 Pa and not more than atmospheric pressure (normal pressure, about 101 kPa). When the step is carried out under a reduced pressure of 10 Pa to 30 kPa, the distillation temperature can be lower, which is more preferred. The distillation temperature in the cases where the step is carried out under reduced pressure is 20° C. to 200° C., but, when the distillation is carried out at a temperature of not less than 180° C., racemization of lactic acid may be caused by the influence of impurities. Therefore, the distillation of lactic acid can be preferably carried out at a temperature of 50° C. to 180° C., more preferably 60° C. to 150° C. Since lactic acid is likely to undergo oligomerization under dehydration conditions (by heating and/or under reduced pressure) because of its structure, the residence time is preferably as short as possible. Accordingly, a film evaporator such as a falling-film evaporator or wiped film evaporator is preferably used as the evaporator since it enables achievement of distillation in a short time and can therefore increase the recovery of lactic acid.

The polylactic acid obtained by polymerization of the lactic acid described above includes a homopolymer of L-lactic acid units or D-lactic acid units; a polylactic acid block copolymer containing a segment composed of a poly-L-lactic acid unit and a segment composed of a poly-D-lactic acid unit; and a copolymer with monomers other than lactic acid. When the polylactic acid is a copolymer, examples of the monomer units other than lactic acid include glycol compounds such as ethylene glycol, propylene glycol, butanediol, heptanediol, hexanediol, octanediol, nonanediol, decanediol, 1,4-cyclohexanedimethanol, neopentyl glycol, glycerin, pentaerythritol, bisphenol A, polyethylene glycol, polypropylene glycol and polytetramethylene glycol; dicarboxylic acids such as oxalic acid, adipic acid, sebacic acid, azelaic acid, dodecanedioic acid, malonic acid, glutaric acid, cyclohexanedicarboxylic acid, terephthalic acid, isophthalic acid, phthalic acid, naphthalenedicarboxylic acid, bis(p-carboxyphenyl)methane, anthracenedicarboxylic acid, diphenyl ether dicarboxylic acid, sodium sulfoisophthalic acid and tetrabutyl phosphonium isophthalic acid; hydroxycarboxylic acids such as glycolic acid, hydroxypropionic acid, hydroxybutyric acid, hydroxyvaleric acid, hydroxycaproic acid and hydroxybenzoic acid; and lactones such as caprolactone, valerolactone, propiolactone, undecalactone and 1,5-oxepan-2-one. The amount of the above-described other copolymerization components to be copolymerized is preferably 0 to 30 mol %, more preferably 0 to 10 mol %, with respect to the total monomer components.

The method of producing the polylactic acid is not restricted, and a general production method for polylactic acid may be used. More specifically, known examples of the method include the two-step lactide method, in which lactide, which is a cyclic dimer, is first produced using lactic acid as a raw material, and ring-opening polymerization is then performed; and the single-step direct polymerization method, in which the raw material is subjected to direct dehydration polycondensation in a solvent. Either method may be used.

In the lactide method and the direct polymerization method, the length of time required for the polymerization can be shortened by using a catalyst for the polymerization reaction. Examples of the catalyst include metals such as tin, zinc, lead, titanium, bismuth, zirconium, germanium, antimony and aluminum, and derivatives thereof. The derivatives are preferably metal alkoxides, carboxylates, carbonates, oxides and halides. Specific examples the derivatives include tin chloride, tin acetate, tin octylate, zinc chloride, lead oxide, lead carbonate, titanium chloride, alkoxytitanium, germanium oxide and zirconium oxide. Among these, tin compounds are preferred, and tin acetate and tin octylate are more preferred.

The polymerization reaction may be carried out in the presence of the above catalyst usually at a temperature of 100 to 200° C., although the temperature varies depending on the type of the catalyst. To remove water produced by the polymerization reaction, the polymerization reaction is preferably carried out under reduced pressure, and the pressure is preferably not more than 7 kPa, more preferably not more than 1.5 kPa.

For the polymerization reaction, a compound having two or more hydroxyl groups or amino groups in the molecule may be used as a polymerization initiator. Examples of the compound to be used as a polymerization initiator, having two or more hydroxyl groups or amino groups in the molecule, include polyols such as ethylene glycol, propylene glycol, butanediol, hexanediol, octanediol, neopentyl glycol, diethylene glycol, triethylene glycol, polyethylene glycol, polypropylene glycol, glycerin, trimethylolpropane, pentaerythritol, dip entaerythritol, trip entaerythritol, sorbitol, poly(vinyl alcohol), poly(hydroxyethyl methacrylate) and poly(hydroxypropyl methacrylate); and polyvalent amines such as ethylenediamine, propylenediamine, butanediamine, hexanediamine, diethylenetriamine and melamine. Among these, polyols are more preferred.

The amount of the polymerization initiator to be added is not limited, and preferably 0.001 to 5 parts by weight, more preferably 0.01 to 3 parts by weight with respect to 100 parts by weight of the raw material used (L-lactic acid, D-lactic acid, L,L-lactide or D,D-lactide).

When the polylactic acid is produced by the direct polymerization method, the solvent to be used is not limited as long as it does not adversely affect the polymerization, and may be water or an organic solvent. Examples of the organic solvent include aromatic hydrocarbons. Examples of the aromatic hydrocarbons include toluene, xylene, naphthalene, chlorobenzene and diphenyl ether. When the polylactic acid is produced by the direct polymerization method, the polymerization can be promoted by removal of water produced by the condensation reaction to the outside of the system. The method of removal to the outside of the system is preferably polymerization under reduced pressure. More specifically, the pressure is preferably not more than 7 kPa, more preferably not more than 1.5 kPa.

EXAMPLES

Our methods are described below in more detail by way of Examples, but this disclosure is not restricted to the Examples below.

Examples 1 to 4

Test for Adsorption Removal of Glycerol Using Ion-Exchange Resin

To 100 g of 90% by weight aqueous lactic acid solution (manufactured by Wako Pure Chemical Industries, Ltd.), 350 g of pure water was added to prepare 20% by weight aqueous lactic acid solution, and the resulting solution was heated to reflux in an oil bath at 120° C. for 5 hours, thereby hydrolyzing lactic acid oligomers in the aqueous solution to provide an aqueous solution of lactic acid monomers. Subsequently, the aqueous lactic acid solution was concentrated using a rotary evaporator, and glycerol was added to the solution such that the glycerol was contained at 5% by weight with respect to lactic acid, to prepare 75% by weight aqueous lactic acid solution containing glycerol. To 20 g of this aqueous lactic acid solution, 2 g of an H-type strong acid ion-exchange resin "Diaion" (registered trademark) SK1BH (manufactured by Mitsubishi Chemical Corporation) (Example 1), 2 g of an Na-type strong acid ion-exchange resin "Diaion" (registered trademark) SK1B (manufactured by Mitsubishi Chemical Corporation) (Example 2), 2 g of a CL-type strong base ion-exchange resin "Amberlite" (registered trademark) IR410JCL (manufactured by The Dow Chemical Company) (Example 3) or 2 g of an OH-type weak base ion-exchange resin "Diaion" (registered trademark) WA20 (manufactured by Mitsubishi Chemical Corporation)

(Example 4) was added, and the resulting mixture was stirred at room temperature for 2 hours at 300 rpm. The glycerol concentration in the aqueous lactic acid solution was measured by high-performance liquid chromatography before and after the ion-exchange resin treatment, and the glycerol adsorption removal rate was calculated according to the method of the Equation 1 below:

Glycerol adsorption removal rate (%)=100×(glycerol concentration before ion-exchange resin treatment (g/L)−glycerol concentration after ion-exchange resin treatment (g/L))/glycerol concentration before ion-exchange resin treatment (g/L)  (Equation 1).

The glycerol concentration in the aqueous lactic acid solution was measured using a high-performance liquid chromatography (manufactured by Shimadzu Corporation) under the following conditions. The results are shown in Table 1.

Column: Shodex NH2P-50 4E (manufactured by Showa Denko K. K.)

Mobile phase: acetonitrile:water=3:1

Flow rate, 0.6 mL/min.

Detection method: differential refractive index detector (RI)

Column temperature, 30° C.

Comparative Example 1

Test for Adsorption Removal of Glycerol Using Activated Carbon

To 100 g of 90% by weight aqueous lactic acid solution (manufactured by Wako Pure Chemical Industries, Ltd.), 350 g of pure water was added to prepare 20% by weight aqueous lactic acid solution, and the resulting solution was heated to reflux in an oil bath at 120° C. for 5 hours, thereby hydrolyzing lactic acid oligomers in the aqueous solution to provide an aqueous solution of lactic acid monomers. Subsequently, the aqueous lactic acid solution was concentrated using a rotary evaporator, and glycerol was added to the solution such that the glycerol was contained at 5% by weight with respect to lactic acid, to prepare 75% by weight aqueous lactic acid solution containing glycerol. To 20 g of this aqueous lactic acid solution, 0.1 g of activated carbon Shirasagi A (manufactured by Japan EnviroChemicals Ltd.) was added, and the resulting mixture was stirred at room temperature for 2 hours at 300 rpm. Thereafter, the activated carbon was separated by filtration using Qualitative Filter Paper No. 2 (manufactured by Advantec), to obtain an aqueous lactic acid solution treated with activated carbon. The glycerol adsorption removal rate after the activated carbon treatment was calculated by the same procedure as in Examples 1 to 4. The results are shown in Table 1.

TABLE 1

| | Adsorbent | Glycerol removal rate (%) |
|---|---|---|
| Example 1 | H-type strong acid ion-exchange resin | 41.2 |
| Example 2 | Na-type strong acid ion-exchange resin | 9.3 |
| Example 3 | CL-type strong base ion-exchange resin | 2.5 |
| Example 4 | OH-type weak base ion-exchange resin | 2.3 |
| Comparative Example 1 | Activated carbon | 0 |

Table 1 shows that, by treating an aqueous lactic acid solution containing glycerol using an ion-exchange resin, an aqueous lactic acid solution in which glycerol is reduced can be obtained, and that strong acid ion-exchange resins have especially high glycerol removal effect.

Examples 5 to 9

Test for Dependence of Glycerol Removal Using Ion-Exchange Resin on Lactic Acid Concentration To 100 g of 90% by weight aqueous lactic acid solution (manufactured by Wako Pure Chemical Industries, Ltd.), 345.5 g of pure water and 4.5 g of glycerol (manufactured by Wako Pure Chemical Industries, Ltd.) were added to prepare 20% by weight aqueous lactic acid solution (glycerol concentration with respect to lactic acid, 5% by weight), and the resulting solution was heated to reflux in an oil bath at 120° C. for 5 hours, thereby hydrolyzing lactic acid oligomers in the aqueous solution to provide an aqueous solution of lactic acid monomers. Subsequently, the aqueous lactic acid solution was concentrated using a rotary evaporator such that the concentration of the aqueous lactic acid solution became 90% by weight (Example 5), 75% by weight (Example 6), 50% by weight (Example 7), 25% by weight (Example 8) or 10% by weight (Example 9). To 20 g of the aqueous lactic acid solution at each concentration, 2 g of an H-type strong acid ion-exchange resin "Diaion" (registered trademark) SK1BH (manufactured by Mitsubishi Chemical Corporation) was added, and the resulting mixture was stirred at room temperature for 2 hours at 300 rpm. The glycerol adsorption removal rate in each sample was calculated by the same procedure as in Examples 1 to 4. The results were as shown in Table 2. It was shown that the higher the lactic acid concentration, that is, the lower the water concentration, the better the glycerol adsorption removal rate.

TABLE 2

| | Lactic acid concentration (%) | Glycerol removal rate (%) |
|---|---|---|
| Example 5 | 90 | 71 |
| Example 6 | 75 | 45 |
| Example 7 | 50 | 20 |
| Example 8 | 25 | 9 |
| Example 9 | 10 | 2 |

Example 10

Test for Removal of Glycerol Using Ion-Exchange Resin Regenerated with Deionized Water To 300 g of 90% by weight aqueous lactic acid solution (manufactured by Wako Pure Chemical Industries, Ltd.), 1050 g of pure water was added to prepare 20% by weight aqueous lactic acid solution, and the resulting solution was heated to reflux in an oil bath at 120° C. for 5 hours, thereby hydrolyzing lactic acid oligomers in the aqueous solution to provide an aqueous solution of lactic acid monomers. Subsequently, the aqueous lactic acid solution was concentrated using a rotary evaporator, and glycerol was added to the solution such that the glycerol was contained at 5% by weight with respect to lactic acid, to prepare 75% by weight aqueous lactic acid solution containing glycerol. To 200 g of this aqueous lactic acid solution, 2 g of an H-type strong acid ion-exchange resin "Diaion" (registered trademark) SK1BH (manufactured by Mitsubishi Chemical Corporation) was added, and the resulting mixture was stirred at room temperature for 2 hours at 300 rpm. The ion-exchange resin was separated by filtration by suction filtration, to obtain an ion-exchange resin to which glycerol was adsorbed. The operation of adding 10 g of deionized water to the recovered ion-exchange resin, stirring the resulting mixture at room temperature for 30 minutes at 300 rpm, and then removing the washing liquid by decantation was repeated twice. To the washed ion-exchange resin, 20 g of 75% by weight aqueous lactic acid solution containing 5% by weight glycerol with respect to lactic acid was newly added, and the resulting mixture was stirred at room temperature for 2 hours at 300 rpm. The glycerol concentration in the aqueous lactic acid solution was measured by high-performance liquid chromatography before and after the ion-exchange resin treatment. As a result, the glycerol removal rate was found to be 40.6%.

Reference Example 1

Test for Removal of Glycerol Using Ion-Exchange Resin (without Regeneration with Deionized Water)

A glycerol removal test was carried out by the same procedure as in Example 10 except that the washing with deionized water was not carried out. The rate of removal of glycerol by the ion-exchange resin treatment was 4.7%.

From the results of Example 10 and Reference Example 1, it was shown that, by subjecting an ion-exchange resin having glycerol adsorbed thereto to washing with deionized water, regeneration of the ion-exchange resin is possible.

Reference Example 2

Production of Lactic Acid by Batch Fermentation

By performing batch fermentation, which is the most typical mode of fermentation using a microorganism, lactic acid productivity by the batch fermentation was evaluated. Using a lactic acid fermentation medium, a batch fermentation test was carried out. The medium was used after autoclaving (121° C. for 15 minutes). As a microorganism, the L-lactic acid fermentation yeast SW-1 strain described in WO2009/004922 was used, and the concentration of lactic acid as a product was evaluated by HPLC as described below:

Column: Shim-Pack SPR-H (manufactured by Shimadzu Corporation)

Mobile phase: 5 mM p-toluenesulfonic acid (flow rate: 0.8 mL/min.)

Reaction solution: 5 mM p-toluenesulfonic acid, 20 mM Bis-Tris, 0.1 mM

EDTA.2Na (flow rate: 0.8 mL/min.)

Detection method: electric conductivity

Temperature: 45° C.

The operation conditions in Reference Example 2 were as shown below:

Reaction vessel capacity (amount of lactic acid fermentation medium): 2 (L)

Temperature adjustment: 30 (° C.)

Reaction vessel ventilation rate: 0.2 (L/min.)

Reaction vessel stirring rate: 400 (rpm)

pH adjustment: adjusted to pH 5 with 1 N calcium hydroxide.

The SW-1 strain was cultured overnight in 5 ml of lactic acid fermentation medium in a test tube (pre-preculture). The pre-cultured medium was inoculated into 100 ml of fresh lactic acid fermentation medium, and culture was performed in a 500-ml Sakaguchi flask for 24 hours with shaking (preculture). Fermentation culture was then performed while the temperature and the pH were adjusted. The amount of the bacteria grown at this time was 15 in terms of the absorbance at 600 nm. The obtained lactic acid fermentation liquid (lactic acid concentration, 30 g/L; glycerol concentration, 1 g/L) was used in the following Examples.

Example 11

Production Example of Lactic Acid Using Lactic Acid Fermented Broth Obtaining Free Lactic Acid by Addition of Acidic Substance Concentrated sulfuric acid (manufactured by Wako Pure Chemical Industries, Ltd.) was added dropwise to 40 L of the culture fermented broth obtained in Reference Example 2 with stirring to a pH of 2.5. The precipitated calcium sulfate was separated by filtration using Qualitative Filter Paper No. 2 (manufactured by Advantec), and the filtrate was collected.

Filtration Through Nanofiltration Membrane

The aqueous lactic acid solution collected as the filtrate was filtered through a nanofiltration membrane module SU-610 (manufactured by Toray Industries, Inc.) at an operating pressure of 2.0 MPa, and the filtrate was collected.

Concentration of Aqueous Lactic Acid Solution

The permeate obtained through the nanofiltration membrane was concentrated using a reverse osmosis membrane module SU-810 (manufactured by Toray Industries, Inc.), and further concentrated by evaporation of water under reduced pressure (50 hPa) using a rotary evaporator (manufactured by Tokyo Rikakikai), to obtain 75% aqueous lactic acid solution. As a result of analyzing the glycerol concentration in the same manner as in Example 1 by high-performance liquid chromatography, the concentration of glycerol with respect to lactic acid was found to be 2.0% by weight.

Adsorption Removal of Glycerol by Ion-Exchange Resin Treatment

To a column packed with 25 mL of a strong acid cation-exchange resin "Diaion" (registered trademark) SK1B (manufactured by Mitsubishi Chemical Corporation) preliminarily prepared as the H type, 500 mL of the concentrated aqueous lactic acid solution was supplied at 2 SV/h, and the eluate was collected. The concentration of glycerol in the aqueous lactic acid solution was measured under the same conditions as in Reference Example 2 by high-performance liquid chromatography (manufactured by Shimadzu Corporation) before and after the ion-exchange resin treatment. As a result, the concentration of glycerol with respect to lactic acid was found to be decreased to 1.2% by weight. From these results, it was found that glycerol can be efficiently reduced by treatment using an ion-exchange resin.

Distillation Under Reduced Pressure

By subjecting 200 g of the aqueous lactic acid solution treated using the ion-exchange resin to distillation under reduced pressure at 133 Pa at 130° C., 156 g of lactic acid was obtained. To the resulting lactic acid, pure water was added to prepare 90% by weight aqueous lactic acid solution. The glycerol concentration in the 90% by weight aqueous lactic acid solution was measured using "F-kit Glycerol" (manufactured by Roche Diagnostics). As a result, the glycerol content in the 90% by weight aqueous lactic acid solution was found to be 17 ppm.

Comparative Example 2

Production Example of Lactic Acid Using Lactic Acid Fermented Broth as Raw Material Lactic acid was produced by the same procedure as in Example 11 except that the adsorption removal of glycerol by ion-exchange resin treatment was not carried out, and, as a result of distillation under reduced pressure, 146 g of lactic acid was obtained. Water was added to the obtained lactic acid to provide 90% by weight aqueous lactic acid solution. The glycerol concentration in the 90% by weight aqueous lactic acid solution was measured using "F-kit Glycerol" (manufactured by Roche Diagnostics) under the same conditions as in Example 11. As a result, the glycerol content in the 90% by weight aqueous lactic acid solution was found to be 72 ppm.

Example 12

Polymerization Test with Lactic Acid, and Evaluation of Physical Properties of Polylactic Acid The 90% by weight aqueous lactic acid solution obtained in Example 11 was subjected to direct dehydration polycondensation, and physical properties of the resulting polylactic acid were analyzed. In a reaction vessel equipped with a stirrer, 150 g of the lactic acid obtained in Example 11 was heated at 800 Pa at 160° C. for 3.5 hours, to obtain oligomers. Subsequently, 0.12 g of tin (II) acetate (manufactured by Kanto Chemical Co., Ltd.) and 0.33 g of methanesulfonic acid (manufactured by Wako Pure Chemical Industries, Ltd.) were added to the oligomers, and the resulting mixture was heated at 500 Pa at 180° C. for 7 hours, to obtain a prepolymer. The prepolymer was then crystallized by heating in an oven at 120° C. for 2 hours. The obtained prepolymer was pulverized using a hammer mill, and passed through a sieve, to obtain pulverulent bodies having an average particle size of 0.1 mm. In the solid phase polymerization step, 150 g of the prepolymer was taken, and fed into an oven to which an oil rotary pump was connected, thereby performing vacuum heat treatment. The pressure was set to 50 Pa, and the heating temperature was set to: 140° C. for 10 hours; 150° C. for 10 hours; and 160° C. for 20 hours. The obtained polylactic acid was subjected to melting point analysis using GDSC (manufactured by SII NanoTechnology Inc.) and thermal weight loss rate analysis using TG (manufactured by SII NanoTechnology Inc.).
Melting Point Analysis of Polylactic Acid
The melting point of the polymerized polylactic acid was measured using a differential scanning calorimeter DSC7020 (manufactured by SII NanoTechnology Inc.) The measurement was carried out with 10 mg of the sample under nitrogen atmosphere at a heating rate of 20° C./minute.
Analysis of Thermal Weight Loss Rate of Polylactic Acid
The thermal weight loss rate of the polymerized polylactic acid was measured using a thermo gravimetry differential thermal analyzer TG/DTA7200 (manufactured by SII Nano-Technology Inc.). The measurement was carried out with 10 mg of the sample under nitrogen atmosphere at a constant temperature of 200° C. for a heating time of 20 minutes. The melting point of the polylactic acid obtained by direct polymerization of lactic acid was 167.3° C., and the thermal weight loss rate was 4.6%.

Comparative Example 3

Polymerization Test of Lactic Acid, and Evaluation of Polymerization of Polylactic Acid By the same procedure as in Example 12 except that the lactic acid obtained in Comparative Example 2 was used, polylactic acid was polymerized and analyzed. The melting point of the obtained polylactic acid was 165.4° C., and the thermal weight loss rate was 6.3%.

From these results, it was shown that the lactic acid in which glycerol is reduced, obtained by our methods, is useful as a raw material for polylactic acid excellent in the melting point and thermostability.

INDUSTRIAL APPLICABILITY

The lactic acid can be suitably used not only for food and pharmaceuticals, but also as a monomer material for polylactic acid, which is a biodegradable plastic. Moreover, the lactic acid can be suitably used as a raw material for polylactic acid excellent in the melting point and thermostability.

The invention claimed is:

1. A method of producing lactic acid comprising removing glycerol from an aqueous lactic acid solution containing glycerol as an impurity using an ion-exchange resin by adsorbing the glycerol to the ion-exchange resin.

2. The method according to claim 1, wherein said ion-exchange resin is a strong acid ion-exchange resin.

3. The method according to claim 1, wherein the lactic acid concentration in said aqueous lactic acid solution is not less than 20% by weight.

4. The method according to claim 1, comprising distilling the aqueous lactic acid solution after removal of glycerol using the ion-exchange resin.

5. The method according to claim 2, wherein the lactic acid concentration in said aqueous lactic acid solution is not less than 20% by weight.

6. The method according to claim 2, comprising distilling the aqueous lactic acid solution after removal of glycerol using the ion-exchange resin.

7. The method according to claim 3, comprising distilling the aqueous lactic acid solution after removal of glycerol using the ion-exchange resin.

* * * * *